(12) United States Patent
Ozturk

(10) Patent No.: US 8,772,537 B2
(45) Date of Patent: Jul. 8, 2014

(54) PROCESS FOR PRODUCING AMINOALKYLTHIOSULFURIC ACID COMPOUND

(75) Inventor: Orhan Ozturk, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 13/808,945

(22) PCT Filed: Jul. 22, 2011

(86) PCT No.: PCT/JP2011/067380
§ 371 (c)(1),
(2), (4) Date: Jan. 8, 2013

(87) PCT Pub. No.: WO2012/015019
PCT Pub. Date: Feb. 2, 2012

(65) Prior Publication Data
US 2013/0116468 A1 May 9, 2013

(30) Foreign Application Priority Data

Jul. 28, 2010 (JP) ................................. 2010-168944
Jul. 28, 2010 (JP) ................................. 2010-168945

(51) Int. Cl.
*C07C 309/00* (2006.01)

(52) U.S. Cl.
USPC ........................................................ 562/36

(58) Field of Classification Search
None
See application file for complete search history.

(56) References Cited

U.S. PATENT DOCUMENTS 4,581,297 A 4/1986 Delseth et al.

FOREIGN PATENT DOCUMENTS

EP 0070143 A1 1/1983
JP 2011-093851 A 5/2011

OTHER PUBLICATIONS

Database Caplus Chemical Abstracts Service, Columbus, Ohio, US; Database Accession No. 1991:449285, Abstract of Chachula et al., Polish Journal of Chemistry (1990), 64(7-12), 619-22.*
Database Caplus Chemical Abstracts Service, Columbus, Ohio, US; Database Accession No. 1990:611692, Abstract of Bulat et al., Khimiko-Farmatsevticheskii Zhurnal (1990), 24(5), 57-9.*
Machine Trasnlation of JP 2011-093851.*
Int'l Preliminary Report on Patentability issued Feb. 5, 2013 in Int'l Application No. PCT/JP2011/067380.
Chachula et al, "Novel Intermediates for Ranitidine Synthesis," Polish Journal of Chemistry, vol. 64, pp. 619-622 (1990).
Bulat et al, "Synthesis of Cystamine," translated from Khimikofarmatsevticheskii Zhurnal, vol. 24, No. 5, pp. 57-59 (May 1990).

* cited by examiner

*Primary Examiner* — Karl J Puttlitz
(74) *Attorney, Agent, or Firm* — Panitch Schwarze Belisario & Nadel LLP

(57) ABSTRACT

An aminoalkylthiosulfuric acid compound represented by formula (1):

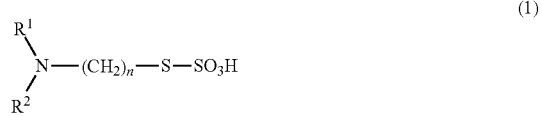

(1)

is produced. In step (A1), a hydrochloride of a chloroalkylamine compound represented by formula (2):

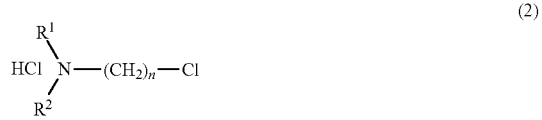

(2)

is reacted with an alkali metal salt of thiosulfuric acid in the presence of 2 to 6 parts by weight of water with respect to 1 part by weight of the hydrochloride between 50° C. and 100° C. $R^1$ and $R^2$ each represents a hydrogen atom and the like, and n represents an integer of 2 to 9. In step (B1), a mixture of a solid containing the aminoalkylthiosulfuric acid compound and a liquid containing an alkali metal chloride is obtained by adjusting the temperature of the mixture of step (A1) to between −15° C. and 50° C. In step (C1), the aminoalkylthiosulfuric acid compound is obtained as solid by separating the solid containing the aminoalkylthiosulfuric acid compound and the liquid containing the alkali metal chloride from the mixture of (B1).

7 Claims, No Drawings

PROCESS FOR PRODUCING AMINOALKYLTHIOSULFURIC ACID COMPOUND

CROSS-REFERENCE TO RELATED APPLICATION

This application is a Section 371 of International Application No. PCT/JP2011/067380, filed Jul. 22, 2011, which was published in the Japanese language on Feb. 2, 2012, under International Publication No. WO 2012/015019 A1, and the disclosure of which is incorporated herein by reference.

TECHNICAL FIELD

The present invention relates to a process for producing an aminoalkylthiosulfuric acid compound.

BACKGROUND ART

U.S. Pat. No. 4,581,297 A describes a method comprising reacting 25 g of hydrobromide of 6-bromohexylamine with 24.2 g of sodium thiosulfate in 580 ml of water, concentrating the obtained reaction solution until its volume was reduced by half, then cooling and isolating the resulting precipitation of S-(6-aminohexyl)thiosulfuric acid by filtering.

DISCLOSURE OF THE INVENTION

The present invention provides
<1> a process for producing an aminoalkylthiosulfuric acid compound represented by formula (1):

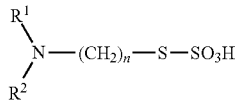

wherein $R^1$ and $R^2$ each independently represent a hydrogen atom or an alkyl group having 1 to 6 carbon atoms, or $R^1$ and $R^2$ are bonded to represent a polymethylene group having 2 to 9 carbon atoms, and n represents an integer of 2 to 9,
the process comprising the following steps (A1), (B1) and (C1):
(A1) a step of reacting a hydrochloride of a chloroalkylamine compound represented by formula (2):

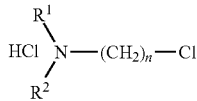

wherein $R^1$, $R^2$ and n are as defined above,
with an alkali metal salt of thiosulfuric acid in the presence of from 2 parts by weight to 6 parts by weight of water with respect to 1 part by weight of the hydrochloride of the chloroalkylamine compound represented by formula (2) at between 50° C. and 100° C.,
(B1) a step of obtaining a mixture of a solid containing the aminoalkylthiosulfuric acid compound represented by formula (1) and a liquid containing an alkali metal chloride by adjusting the temperature of the reaction mixture obtained in step (A1) to not lower than −15° C. and lower than 50° C.,
(C1) a step of obtaining the aminoalkylthiosulfuric acid compound as solid by separating the solid containing the aminoalkylthiosulfuric acid compound represented by formula (1) and the liquid containing the alkali metal chloride from the mixture obtained in step (B1);
<2> The process according to <1>, wherein the amount of the water in step (A1) is from 2.5 parts by weight to 4 parts by weight with respect to 1 part by weight of the hydrochloride of the chloroalkylamine compound represented by formula (2);
<3> The process according to <1> or <2>, wherein the used amount of the alkali metal salt of thiosulfuric acid in step (A1) is from 0.9 mole to 1.5 moles with respect to 1.0 mole of the hydrochloride of the chloroalkylamine compound represented by formula (2);
<4> The process according to each one of <1> to <3>, wherein step (B1) is a step of obtaining a mixture of a solid containing the aminoalkylthiosulfuric acid compound represented by formula (1) and a liquid containing an alkali metal chloride by adjusting the temperature of the reaction mixture obtained in step (A1) to not lower than −15° C. and not higher than 30° C.;
<5> A process for producing an aminoalkylthiosulfuric acid compound represented by formula (1):

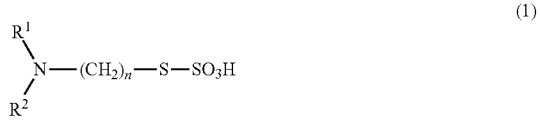

wherein $R^1$ and $R^2$ each independently represent a hydrogen atom or an alkyl group having 1 to 6 carbon atoms, or $R^1$ and $R^2$ are bonded to represent a polymethylene group having 2 to 9 carbon atoms, and n represents an integer of 2 to 9,
the process comprising the following steps (A2), (B2), (C2) and (D2):
(A2) a step of obtaining a mixture of a solid containing an alkali metal chloride and a liquid containing an aminoalkylthiosulfuric acid compound represented by formula (1) by reacting a hydrochloride of chloroalkylamine compound represented by formula (2):

wherein $R^1$, $R^2$ and n are as defined above,
with an alkali metal salt of thiosulfuric acid in the presence of not less than 1 part by weight and less than 2 parts by weight of water with respect to 1 part by weight of the hydrochloride of the chloroalkylamine compound represented by formula (2) at between 50° C. and 100° C.,
(B2) a step of separating the solid containing the alkali metal chloride and the liquid containing the aminoalkylthiosulfuric acid compound represented by formula (1) from the mixture obtained in step (A2),
(C2) a step of obtaining a mixture of a solid containing the aminoalkylthiosulfuric acid compound represented by formula (1) and a liquid containing water by adjusting the temperature of the liquid containing the aminoalkylthiosulfuric acid compound represented by formula (1) and obtained in step (B2) to not lower than −15° C. and lower than 50° C., (D2) a step of obtaining the aminoalkylthiosulfuric acid compound as solid by separating the solid containing the aminoalkylthiosulfuric acid compound represented by formula (1) and the liquid containing water from the mixture obtained in step (C2);

<6> The process according to <5>, wherein the used amount of the alkali metal salt of thiosulfuric acid in step (A2) is from 0.9 mole to 1.5 moles with respect to 1.0 mole of the hydrochloride of the chloroalkylamine compound represented by formula (2);

<7> The process according to <5> or <6>, wherein step (C2) is a step of obtaining a mixture of a solid containing the aminoalkylthiosulfuric acid compound represented by formula (1) and a liquid containing water by adjusting the temperature of the liquid containing the aminoalkylthiosulfuric acid compound represented by formula (1) and obtained in step (B2) to not lower than −15° C. and not higher than 30° C.

BEST MODE FOR CARRYING OUT THE INVENTION

The first embodiment of the present invention is the process for producing an aminoalkylthiosulfuric acid compound represented by formula (1) (hereinafter referred to as compound (1)):

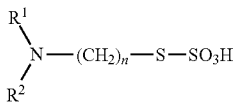

(1)

wherein $R^1$ and $R^2$ each independently represent a hydrogen atom or an alkyl group having 1 to 6 carbon atoms, or $R^1$ and $R^2$ are bonded to represent a polymethylene group having 2 to 9 carbon atoms, and n represents an integer of 2 to 9, the process comprising the following steps (A1), (B1) and (C1):

(A1) a step of reacting a hydrochloride of a chloroalkylamine compound represented by formula (2) (hereinafter referred to as compound (2)):

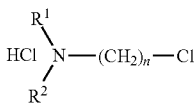

(2)

wherein $R^1$, $R^2$ and n are as defined above, with an alkali metal salt of thiosulfuric acid in the presence of from 2 parts by weight to 6 parts by weight of water with respect to 1 part by weight of compound (2) at between 50° C. and 100° C., (B1) a step of obtaining a mixture of a solid containing compound (1) and a liquid containing an alkali metal chloride by adjusting the temperature of the reaction mixture obtained in step (A1) to not lower than −15° C. and lower than 50° C., (C1) a step of obtaining compound (1) as solid by separating the solid containing compound (1) and the liquid containing the alkali metal chloride from the mixture obtained in step (B1).

First, step (A1) will be explained. Step (A1) is a step of reacting compound (2) with an alkali metal salt of thiosulfuric acid in the presence of from 2 parts by weight to 6 parts by weight of water with respect to 1 part by weight of compound (2) at between 50° C. and 100° C.

Examples of the alkyl group having 1 to 6 carbon atoms represented by $R^1$ and $R^2$ include a linear or branched alkyl group having 1 to 6 carbon atoms such as a methyl group, an ethyl group, a propyl group, an isopropyl group, a butyl group, a sec-butyl group, a tert-butyl group, a pentyl group and a hexyl group.

Examples of the polymethylene group having 2 to 6 carbon atoms formed by bonding $R^1$ and $R^2$ include an ethylene group (a dimethylene group), a trimethylene group, a tetramethylene group, a pentamethylene group and hexamethylene group.

$R^1$ and $R^2$ are preferably hydrogen atoms.

Examples of compound (2) include a hydrochloride of 2-chloroethylamine, a hydrochloride of 3-chloropropylamine, a hydrochloride of 4-chlorobutylamine, a hydrochloride of 5-chloropentylamine, a hydrochloride of 6-chlorohexylamine, a hydrochloride of 1-chloro-3-(methylamino)propane, hydrochloride of 1-chloro-3-(ethylamino)propane, a hydrochloride of 1-chloro-3-(dimethylamino)propane, and a hydrochloride of 1-chloro-3-piperidinopropane.

There can be used as compound (2) either a commercially available product or a product produced by, for example, the method comprising contacting an alcohol compound represented by formula (3):

$$H_2N-(CH_2)_n-OH \qquad (3)$$

wherein n represent an integer of 2 to 9, with thionyl chloride, or a method comprising reacting a dichloroalkane with a potassium salt of phthalimide, and then contacting the obtained compound with hydradine or a primary amine can be used.

Examples of the alkali metal salt of thiosulfuric acid include lithium thiosulfate, sodium thiosulfate, potassium thiosulfate, rubidium thiosulfate and cesium thiosulfate, and among them, preferred are sodium thiosulfate and potassium thiosulfate, more preferred is sodium thiosulfate. The alkali metal salt of thiosulfuric acid may be an anhydrate or a hydrate.

The used amount of the alkali metal salt of thiosulfuric acid is usually not less than 0.9 mole with respect to 1.0 mole of compound (2), preferably from 0.9 mole to 1.5 moles, more preferably from 1.0 mole to 1.1 moles.

The reaction of compound (2) and the alkali metal salt of thiosulfuric acid is conducted in the presence of from 2 parts by weight to 6 parts by weight of water with respect to 1 part by weight of compound (2). When a hydrate of the alkali metal salt of thiosulfuric acid is used as the alkali metal salt of thiosulfuric acid, the water includes water contained in the hydrate. When the used amount of water is not less than 2 parts by weight with respect to 1 part by weight of compound (2), the precipitation of the alkali metal chloride can be inhibited in step (B1) described below. When the used amount of water is not more than 6 parts by weight with respect to 1 part by weight of compound (2), the precipitation of compound (1) can be accelerated in step (B1) described below. The reaction of compound (2) and the alkali metal salt of thiosulfuric acid is preferably conducted in the presence of from 2.5 parts by weight to 4 parts by weight of water with respect to 1 part by weight of compound (2).

The reaction of compound (2) and the alkali metal salt of thiosulfuric acid is conducted at between 50° C. and 100° C., preferably from 60° C. to 100° C., more preferably from 70° C. to 100° C. The reaction time is usually in the range of from 10 minutes to 24 hours. The progress of the reaction can be checked by usual analysis means, such as thin-layer chromatography, high performance liquid chromatography and $^1$H-NMR.

Next, step (B1) will be explained. Step (B1) is a step of obtaining a mixture of a solid containing compound (1) and a liquid containing an alkali metal chloride by adjusting the temperature of the reaction mixture obtained in step (A1) to not lower than −15° C. and lower than 50° C.

The reaction mixture obtained in step (A1) may be used in step (B1) as it is, or may be used in step (B1) after partially concentration thereof or after addition of water thereto. Usually the reaction mixture obtained in step (A1) is used in step (B1) as it is.

By adjusting the temperature of the reaction mixture obtained in step (A1) to not lower than −15° C. and lower than 50° C., preferably not lower than −15° C. and not higher than 30° C., compound (1) can be precipitated. When the temperature of the reaction mixture obtained in step (A1) is adjusted to not lower than −15° C., the precipitation of the alkali metal chloride can be inhibited and handleability is good. When the temperature of the reaction mixture obtained in step (A1) is adjusted to lower than 50° C., the precipitation of compound (1) can be accelerated. The balance of the amount of the precipitation of compound (1) and the amount of the precipitation of the alkali metal chloride can be adjusted in desired range by lowering the temperature within the range of not lower than −15° C. and lower than 50° C. when the amount of the precipitation of compound (1) is not enough, or by raising the temperature within the range of not lower than −15° C. and lower than 50° C. when much alkali metal chloride has precipitated.

Thus, the mixture of the solid mainly containing compound (1) and the liquid containing the alkali metal chloride can be obtained.

In step (A1) and (B1), an organic solvent may be used. When the organic solvent is used, the amount of the precipitation of compound (1) decrease or the alkali metal chloride is precipitated. Therefore, it is preferred the used amount of the organic solvent is small, and it is more preferred that no organic solvent is used.

Subsequently, step (C1) will be explained. Step (C1) is a step of obtaining the aminoalkylthiosulfuric acid compound as solid by separating the solid containing compound (1) and the liquid containing the alkali metal chloride from the mixture obtained in step (B1).

The mixture obtained in step (B1) may be used in step (C1) as it is or may be used after partially concentration thereof or after addition of water thereto. Usually, the mixture obtained in step (B1) may be used in step (C1) as it is The separation of the solid containing compound (1) and the liquid containing the alkali metal chloride is usually conducted at the same range of temperature as that in step (B1). The separation is carried out by usual solid-liquid separation means, such as filtration and decantation.

The separated solid comprising compound (1) may be washed with water, a water-soluble organic solvent (for example, an alcohol solvent such as methanol and ethanol) and the like. The obtained solid may be dried as necessary.

Examples of compound (1) contained in thus obtained solid include S-(2-aminoethyl)thiosulfuric acid, S-(3-aminopropyl)thiosulfuric acid, S-(4-aminobutyl)thiosulfuric acid, S-(5-aminopentyl)thiosulfuric acid, S-(6-aminohexyl)thiosulfuric acid, S-(3-methylaminopropyl)thiosulfuric acid, S-(3-ethylaminopropyl)thiosulfuric acid, S-(3-dimethylaminopropyl)thiosulfuric acid, and S-(3-piperidinopropyl)thiosulfuric acid.

Subsequently, the second embodiment of the present invention will be explained. The second embodiment of the present invention is a process for producing compound (1) comprising the following steps (A2), (B2), (C2) and (D2).

(A2) a step of obtaining a mixture of a solid containing an alkali metal chloride and a liquid containing compound (1) by reacting compound (2) with an alkali metal salt of thiosulfuric acid in the presence of not less than 1 part by weight and less than 2 parts by weight of water with respect to 1 part by weight of compound (2) at between 50° C. and 100° C., (B2) a step of separating the solid containing the alkali metal chloride and the liquid containing compound (1) from the mixture obtained in step (A2), (C2) a step of obtaining a mixture of a solid containing compound (1) and a liquid containing water by adjusting the temperature of the liquid containing compound (1) and obtained in step (B2) to not lower than −15° C. and lower than 50° C., (D2) a step of obtaining compound (1) as solid by separating the solid containing compound (1) and the liquid containing water from the mixture obtained in step (C2).

Step (A2) is a, step of obtaining a mixture of a solid containing an alkali metal chloride and a liquid containing compound (1) by reacting compound (2) with an alkali metal salt of thiosulfuric acid in the presence of not less than 1 part by weight and less than 2 parts by weight of water with respect to 1 part by weight of compound (2) at between 50° C. and 100° C.

Examples of compound (2) include the same compounds as described above.

Examples of the alkali metal salt of thiosulfuric acid include the same salts as described above.

The used amount of the alkali metal salt of thiosulfuric acid is usually not less than 0.9 mole with respect to 1.0 mole of compound (2), preferably from 0.9 mole to 1.5 moles, more preferably from 1.0 mole to 1.1 moles.

The reaction of compound (2) and the alkali metal salt of thiosulfuric acid is conducted in the presence of not less than 1 part by weight and less than 2 parts by weight of water with respect to 1 part by weight of compound (2). When the used amount of water is not less than 1 part by weight with respect to 1 part by weight of compound (2), the precipitation of compound (1) can be inhibited in step (A2). When the used amount of water is less than 2 parts by weight with respect to 1 part by weight of compound (2), the precipitation of the alkali metal chloride can be accelerated in step (A2).

The reaction of compound (2) and the alkali metal salt of thiosulfuric acid is conducted at between 50° C. and 100° C., preferably from 60° C. to 100° C., more preferably from 70° C. to 100° C. The reaction time is usually in the range of from 10 minutes to 24 hours. The progress of the reaction can be checked by usual analysis means, such as thin-layer chromatography, high performance liquid chromatography and $^1$H-NMR.

Step (B2) is a step of separating the solid containing the alkali metal chloride and the liquid containing compound (1) from the mixture obtained in step (A2).

The mixture obtained in step (A2) may be used in step (B2) as it is, or may be used after partially concentration thereof or after addition of water thereto. Usually the mixture obtained in step (A2) is used in step (B2) as it is.

The separation of the solid containing the alkali metal chloride and the liquid containing compound (1) is conducted at the same range of temperature as that in step (A2). The separation is conducted by usual solid-liquid separation means, such as filtration and decantation.

The solid thus obtained may be washed with water. Compound (1) attaching to the solid can be recovered as an aqueous solution by the washing.

Step (C2) is a step of obtaining a mixture of a solid containing compound (1) and a liquid containing water by adjusting the temperature of the liquid containing compound (1) and obtained in step (B2) to not lower than −15° C. and lower than 50° C.

The liquid containing compound (1) and obtained in step (B2) may be used in step (C2) as it is, or may be used after partially concentration thereof or after addition of water thereto. Usually the liquid containing compound (1) and obtained in step (B2) may be used in step (C2) as it is.

By adjusting the temperature of the liquid containing compound (1) and obtained in step (B2) to not lower than −15° C. and lower than 50° C., preferably not lower than −15° C. and not higher than 30° C., compound (1) can be precipitated. When the temperature of the liquid containing compound (1) and obtained in step (B2) is not lower than −15° C., the precipitation of the alkali metal chloride can be inhibited and handleability is good in the case the alkali metal chloride is contained in the liquid. When the temperature of the liquid containing compound (1) and obtained in step (B2) is lower than 50° C., the precipitation of compound (1) can be accelerated. The balance of the amount of the precipitation of compound (1) and the amount of the precipitation of the alkali metal chloride can be adjusted in desired range by lowering the temperature within the range of not lower than −15° C. and lower than 50° C. when the precipitation of compound (1) is not enough, by raising the temperature within the range of not lower than −15° C. and lower than 50° C. when the precipitation of the alkali metal chloride is increased.

Thus, the mixture of the solid mainly containing compound (1) and the liquid containing water can be obtained.

In step (A2), (B2) and (C2), an organic solvent may be used. Preferably, the used amount of the organic solvent is small, and more preferably no organic solvent is used because the amount of the precipitation of compound (1) becomes small or the alkali metal chloride is precipitated.

Step (D2) is a step of obtaining compound (1) as solid by separating the solid containing compound (1) and the liquid containing water from the mixture obtained in step (C2).

The mixture obtained in step (C2) may be used in step (D2) as it is, or may be used after partially concentration thereof or after addition of water thereto. Usually the mixture obtained in step (C2) may be used in step (D2) as it is.

The separation of the solid containing compound (1) and the liquid containing the alkali metal chloride is conducted at the same range of temperature as that in step (C2). The separation is conducted by usual solid-liquid separation means, such as filtration and decantation.

The separated solid comprising compound (1) may be washed with water, a water-soluble organic solvent (for example, an alcohol solvent such as methanol and ethanol) and the like. The obtained solid may be dried as necessary.

Examples of compound (1) comprised in the solid include the same compounds as described above.

Example 1

In the reaction vessel purged with nitrogen, 100 g (0.77 mole) of hydrochloride of 3-chloropropylamine was added, and 180 mL of water was further added thereto to dissolve the hydrochloride of 3-chloropropylamine. To the obtained solution was added 200.4 g (0.81 mole) of pentahydrate of sodium thiosulfate, and then the obtained aqueous solution was kept at 60° C. to 70° C., and the solution was stirred while the reaction vessel was heated at a bath temperature of 80° C. After the solution was stirred at a bath temperature of 80° C. for 4 hours, the completion of the reaction was checked by $^1$H-NMR measurement. After the solution was stirred at a bath temperature of 80° C. for 5 hours in total, the solution was cooled.

The obtained reaction mixture was stirred overnight at room temperature (from about 20° C. to about 25° C.), so that the solid mainly containing S-(3-aminopropyl)thiosulfuric acid was precipitated. The obtained mixture was filtrated to afford the solid mainly containing S-(3-aminopropyl)thiosulfuric acid.

The obtained solid was washed with a small amount of water and then 50 mL of methanol, and then dried at 50° C. for 4 hours.

The acquisition amount of the solid mainly containing S-(3-aminopropyl)thiosulfuric acid was 97.8 g. The concentration of chloride ion (Cl$^-$) in the obtained solid was measured by ion chromatography and was found to be 0.56% (0.92 weight % in sodium chloride equivalent). The acquisition rate of S-(3-aminopropyl)thiosulfuric acid was 73.6%

Herein, the acquisition rate of S-(3-aminopropyl)thiosulfuric acid means the yield of S-(3-aminopropyl)thiosulfuric acid calculated by using the acquisition amount of S-(3-aminopropyl)thiosulfuric acid defined by the amount obtained by subtracting the amount of sodium chloride from the acquisition amount of the solid mainly containing S-(3-aminopropyl)thiosulfuric acid.

Examples 2 and 4, and Reference Examples 1 and 2

The same procedure as that used in Example 1 was carried out except that the amount of the water used in the reaction of hydrochloride of 3-chloropropylamine and pentahydrate of sodium thiosulfate was changed to that provided in Table 1-1 and Table 1-2, and the temperature of stirring overnight the reaction mixture obtained by the reaction of hydrochloride of 3-chloropropylamine and pentahydrate of sodium thiosulfate were changed to that provided in Table 1-1 and Table 1-2, affording the solid mainly containing S-(3-aminopropyl)thiosulfuric acid.

The results are provided in Table 1-1 and Table 1-2 together with that of Example 1. In Table 1-1 and Table 1-2, hydrochloride of 3-chloropropylamine is denoted as compound (2a) and S-(3-aminopropyl)thiosulfuric acid is denoted as compound (1a).

Example 3

In the reaction vessel purged with nitrogen, 100 g (0.77 mole) of hydrochloride of 3-chloropropylamine was added, and 200 mL of water was further added thereto to dissolve hydrochloride of 3-chloropropylamine. To the obtained solution was added 200.4 g (0.81 mole) of pentahydrate of sodium thiosulfate at room temperature (from about 20° C. to about 25° C.), then the solution was stirred while the reaction vessel was heated at a bath temperature of 70° C. After the solution was stirred at a bath temperature of 70° C. for 7 hours, $^1$H-NMR measurement was revealed that the residual amount of 3-chloropropylamine was not more than 1%.

The reaction mixture was cooled to room temperature (from about 20° C. to about 25° C.), then stirred overnight. Furthermore, the reaction mixture was cooled to −10° C. and stirred for 1.5 hours to precipitate the solid mainly containing S-(3-aminopropyl)thiosulfuric acid. The obtained mixture was filtrated to afford the precipitated solid.

The obtained solid was washed with 60 mL of cold water and then 40 mL of methanol, and then dried at 50° C. under reduced pressure.

The acquisition amount of the solid was 108.1 g. The concentration of chloride ion (Cl⁻) in the obtained solid was measured by ion chromatography and was found to be 0.08% (0.13 weight % in sodium chloride equivalent). The acquisition rate of S-(3-aminopropyl)thiosulfuric acid was 81.9%

Example 5

The same procedure as that used in Example 3 was carried out except that the amount of the water used in the reaction of hydrochloride of 3-chloropropylamine and pentahydrate of sodium thiosulfate was changed to that provided in Table 1-1 and Table 1-2, and the temperature of stirring overnight the reaction mixture obtained by the reaction of hydrochloride of 3-chloropropylamine and pentahydrate of sodium thiosulfate were changed to that provided in Table 1-1 and Table 1-2, affording the solid mainly containing S-(3-aminopropyl)thiosulfuric acid. The results are provided in Table 1-1 and Table 1-2 together with that of Example 3.

TABLE 1-1

|  | Example | | | |
| --- | --- | --- | --- | --- |
|  | 1 | 2 | 3 | 4 |
| Used amount of water (g) | 180 | 200 | 200 | 250 |
| Water contained in pentahydrate of sodium thiosulfate (g) | 72 | 72 | 72 | 72 |
| Total used amount of water(g) | 252 | 272 | 272 | 322 |
| Weight rate of water/compound (2a) | 2.52 | 2.72 | 2.72 | 3.22 |
| Temperature | (1) | (1) | −10° C. | (1) |
| Acquisition amount of the solid (g) | 97.8 | 85.0 | 108.1 | 74.6 |
| Cl⁻ concentration in the solid (%) | 0.56 | 0.08 | 0.08 | 0.02 |
| NaCl in the solid (weight %) | 0.92 | 0.13 | 0.13 | 0.03 |
| Acquisition rate of compound (1a) (%) | 73.6 | 64.5 | 81.9 | 56.6 |

(1) Room temperature(from about 20° C. to about 25° C.)

TABLE 1-2

|  | Example | Reference example | |
| --- | --- | --- | --- |
|  | 5 | 1 | 2 |
| Used amount of water (g) | 500 | 100 | 1000 |
| Water contained in pentahydrate of sodium thiosulfate (g) | 72 | 72 | 72 |
| Total used amount of water (g) | 572 | 172 | 1072 |
| Weight rate of water/compound (2a) | 5.72 | 1.72 | 10.72 |
| Temperature | −9° C. | (1) | (2) |
| Acquisition amount of the solid (g) | 98.4 | 130 | 0 (#) |
| Cl⁻ concentration in the solid (%) | 0.07 | 10.4 | — |
| NaCl in the solid (weight %) | 0.12 | 17.16 | — |

TABLE 1-2-continued

|  | Example | Reference example | |
| --- | --- | --- | --- |
|  | 5 | 1 | 2 |
| Acquisition rate of compound (1a) (%) | 74.6 | 81.8 | — |

(1) Room temperature(from about 20° C. to about 25° C.)
(2) About 4° C. (refrigerator)
(#) The precipitation of the solid was not observed after keeping in the refrigerator at about 4° C. for 16 hours.

Example 6

In the reaction vessel purged with nitrogen, 600 g (4.61 moles) of hydrochloride of 3-chloropropylamine was added, and 1200 mL of water was further added thereto to dissolve hydrochloride of 3-chloropropylamine. The pH of the obtained aqueous solution was 2.8. The obtained aqueous solution was kept at from 60° C. to 70° C., and 1200 g (4.84 moles) of pentahydrate of sodium thiosulfate was added thereto. The total used amount of water was 1632 g (the total of 1200 g of water and 432 g of water contained in pentahydrate of sodium thiosulfate). At this point, the pH of the aqueous solution was from 5 to 5.5. The solution was stirred for 4 hours while the reaction vessel was heated at a bath temperature of 80° C. At this stage, the precipitation of the crystal was not observed. The obtained reaction mixture was cooled, then the crystal started to precipitate from a inner temperature of about 45° C. After that, the obtained mixture was stirred overnight at room temperature (about from 20° C. to 25° C.). At this point, the pH of the liquid phase was from 2.5 to 2.8. After that, the inner temperature was adjusted to about 5° C. by cooling the reaction vessel with iced water to precipitate the solid mainly containing S-(3-aminopropyl)thiosulfuric acid.

The obtained mixture was filtrated to afford the solid mainly containing S-(3-aminopropyl)thiosulfuric acid.

The obtained solid was washed with 100 mL of water and then 500 mL of methanol, and then dried with an evaporator (using diaphragm pump) at a bath temperature of 50 to 55° C. for about 1 hour, and furthermore, dried by the vacuum pump for 4 hours.

The acquisition amount of the solid mainly containing S-(3-aminopropyl)thiosulfuric acid was 627.9 g. The concentration of chloride ion in the obtained solid was measured by ion chromatography and was found to be 0.02% (0.03% in sodium chloride equivalent). The amount of the water in the solid was measured with the moisture vaporization—coulometric titration and was found to be 0.01%. The acquisition rate of S-(3-aminopropyl)thiosulfuric acid was 79.4%

Example 7

In the reaction vessel purged with nitrogen, 580 g (4.47 moles) of hydrochloride of 3-chloropropylamine was added, and 1048 mL of water was further added thereto to dissolve hydrochloride of 3-chloropropylamine. The obtained solution was kept at from 60° C. to 70° C., and 1164 g (4.69 moles) of pentahydrate of sodium thiosulfate was added thereto. The total used amount of water was 1470 g (the total of 1048 g of water and 422 g of water contained in pentahydrate of sodium thiosulfate). The solution was stirred for 4 hours while the reaction vessel was heated at a bath temperature of 80° C. After 2 hours, a little amount of solid was precipitated. The obtained reaction mixture was cooled, and then stirred overnight at room temperature. The obtained mixture was filtrated to afford the solid mainly containing S-(3-aminopropyl)thiosulfuric acid.

The obtained solid was washed with 100 mL of water and then 500 mL of methanol, and then dried by an evaporator (using diaphragm pump) at a bath temperature of from 50 to 55° C. for about 1 hour, and furthermore, dried by the vacuum pump for 4 hours.

The acquisition amount of the solid mainly containing S-(3-aminopropyl)thiosulfuric acid was 556.6 g. The concentration of chloride ion in the obtained solid was measured by ion chromatography and was found to be 0.88% (1.45% in sodium chloride equivalent). The amount of the water in the solid was measured with the moisture vaporization—coulometric titration and was found to be 0.02%. The acquisition rate of S-(3-aminopropyl)thiosulfuric acid was 71.7%

Example 8

In the reaction vessel purged with nitrogen, 99.26 g (0.76 mole) of a hydrochloride of 3-chloropropylamine was added, and 100 mL of water was further added thereto to dissolve hydrochloride of 3-chloropropylamine. To the obtained solution was added 199.0 g (0.81 mole) of pentahydrate of sodium thiosulfate at room temperature. Then the solution was stirred while the reaction vessel was heated at a bath temperature of 70° C. The solution was stirred at a bath temperature of 70° C. for 6.5 hours. The obtained mixture was filtrated at the same temperature to afford the precipitated solid. The acquisition amount of the solid was 35.8 g. The solid was measured with $^1$H-NMR measurement to find out that 2.9 g of S-(3-aminopropyl)thiosulfuric acid was contained in the solid.

The obtained filtrate was cooled to 5° C. and stirred for 1.5 hours, then the solid mainly containing S-(3-aminopropyl)thiosulfuric acid precipitated. The obtained mixture was filtrated to afford the solid mainly containing S-(3-aminopropyl)thiosulfuric acid.

The obtained solid was washed with 60 mL of cold water and then 40 mL of methanol, and then dried under reduced pressure at 50° C.

The acquisition amount of the solid mainly containing S-(3-aminopropyl)thiosulfuric acid was 100.8 g. The concentration of chloride ion in the obtained solid was measured by ion chromatography and was found to be 0.03% (0.05 weight % in sodium chloride equivalent). The acquisition rate of S-(3-aminopropyl)thiosulfuric acid was 77.1%

Example 9

The same procedure as that used in Example 8 was carried out except that the obtained filtrate was cooled to −4° C., to obtain the solid mainly containing S-(3-aminopropyl)thiosulfuric acid.

The concentration of chloride ion in the obtained solid was measured by ion chromatography and was found to be 0.04% (0.07 weight % in sodium chloride equivalent). The acquisition rate of S-(3-aminopropyl)thiosulfuric acid was 79.6%

INDUSTRIAL APPLICABILITY

According to the present invention, an aminoalkylthiosulfuric acid compound can be produced efficiently.

The invention claimed is:

1. A process for producing S-(3-aminopropyl)thiosulfuric acid, the process comprising the following steps (A1), (B1) and (C1):

(A1) a step of reacting a hydrochloride of 3-chloropropylamine
with an alkali metal salt of thiosulfuric acid in the presence of from 2.72 parts by weight to 6 parts by weight of water with respect to 1 part by weight of the hydrochloride of 3-chloropropylamine at between 50° C. and 100° C., (B1) a step of obtaining a mixture of a solid containing S-(3-aminopropyl)thiosulfuric acid and a liquid containing an alkali metal chloride by adjusting the temperature of the reaction mixture obtained in step (A1) to not lower than −15° C. and lower than 50° C., and (C1) a step of obtaining S-(3-aminopropyl)thiosulfuric acid as a solid by separating the solid containing S-(3-aminopropyl)thiosulfuric acid and the liquid containing the alkali metal chloride from the mixture obtained in step (B1).

2. The process according to claim 1, wherein the amount of the water in step (A1) is from 2.72 parts by weight to 4 parts by weight with respect to 1 part by weight of the hydrochloride of 3-chloropropylamine.

3. The process according to claim 1, wherein the used amount of the alkali metal salt of thiosulfuric acid in step (A1) is from 0.9 mole to 1.5 moles with respect to 1.0 mole of the hydrochloride of 3-chloropropylamine.

4. The process according to claim 1, wherein step (B1) is a step of obtaining a mixture of a solid containing S-(3-aminopropyl)thiosulfuric acid and a liquid containing an alkali metal chloride by adjusting the temperature of the reaction mixture obtained in step (A1) to not lower than −15° C. and not higher than 30° C.

5. A process for producing an aminoalkylthiosulfuric acid compound represented by formula (1):

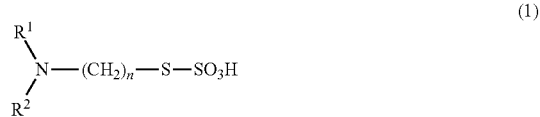

(1)

wherein $R^1$ and $R^2$ each independently represent a hydrogen atom or an alkyl group having 1 to 6 carbon atoms, or $R^1$ and $R^2$ are bonded to represent a polymethylene group having 2 to 9 carbon atoms, and n represents an integer of 2 to 9, the process comprising the following steps (A2), (B2), (C2) and (D2):

(A2) a step of obtaining a mixture of a solid containing an alkali metal chloride and a liquid containing an aminoalkylthiosulfuric acid compound represented by formula (1) by reacting a hydrochloride of chloroalkylamine compound represented by formula (2):

(2)

wherein $R^1$, $R^2$ and n are as defined above,
with an alkali metal salt of thiosulfuric acid in the presence of not less than 1 part by weight and less than 2 parts by weight of water with respect to 1 part by weight of the hydrochloride of the chloroalkylamine compound represented by formula (2) at between 50° C. and 100° C., (B2) a step of separating the solid containing the alkali metal chloride and the liquid containing the aminoalkylthiosulfuric acid compound represented by formula (1) from the mixture obtained in step (A2), (C2) a step of obtaining a mixture of a solid containing the aminoalkylthiosulfuric acid compound represented by formula (1) and a liquid containing water by adjusting the temperature of the liquid containing the aminoalkylthiosulfuric acid compound represented by formula (1) and obtained in step (B2) to not lower than −15° C. and lower than 50° C., (D2) a step of obtaining the aminoalkylthiosulfuric acid compound as solid by separating the solid containing the aminoalkylthiosulfuric acid compound represented by formula (1) and the liquid containing water from the mixture obtained in step (C2).

6. The process according to claim 5, wherein the used amount of the alkali metal salt of thiosulfuric acid in step (A2) is from 0.9 mole to 1.5 moles with respect to 1.0 mole of the hydrochloride of the chloroalkylamine compound represented by formula (2).

7. The process according to claim 5, wherein step (C2) is a step of obtaining a mixture of a solid containing the aminoalkylthiosulfuric acid compound represented by formula (1) and a liquid containing water by adjusting the temperature of the liquid containing the aminoalkylthiosulfuric acid compound represented by formula (1) and obtained in step (B2) to not lower than −15° C. and not higher than 30° C.

* * * * *